United States Patent
Egger et al.

(10) Patent No.: US 6,599,473 B1
(45) Date of Patent: Jul. 29, 2003

(54) ELECTROCHEMILUMISCENCE METHOD FOR DETECTING ANALYTES

(75) Inventors: Martin Egger, Bernried (DE); Gabriele Punzmann, Munich (DE); Guenter Mueller, Peissenberg (DE); Ursula Pauselius-Fuchs, Starnberg (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/600,663
(22) PCT Filed: Jan. 23, 1999
(86) PCT No.: PCT/DE99/00197
§ 371 (c)(1),
(2), (4) Date: Dec. 4, 2000
(87) PCT Pub. No.: WO99/39206
PCT Pub. Date: Aug. 5, 1999

(30) Foreign Application Priority Data

Jan. 30, 1998 (DE) .......................... 198 03 528

(51) Int. Cl.[7] ...................... G01N 21/76; G01N 33/536; G01N 27/26; G01N 33/60
(52) U.S. Cl. .................. 422/52; 436/536; 436/526; 436/172; 436/805; 436/806; 435/968; 435/7.1; 204/402; 204/403.01; 205/775; 205/777.5
(58) Field of Search ................. 436/527–533, 436/536, 164, 172, 805, 806; 435/7.1, 968; 204/402, 403.01; 205/775, 777.5; 422/52

(56) References Cited

U.S. PATENT DOCUMENTS 4,917,777 A * 4/1990 Fisher ..................... 204/153.1
5,746,974 A * 5/1998 Massey et al. ................ 422/52
5,779,976 A * 7/1998 Leland et al. ................. 422/52

FOREIGN PATENT DOCUMENTS

| EP | 0 647 849 A2 | 4/1995 | ......... G01N/33/543 |
| WO | WO 89/10551 | 11/1989 | ......... G01N/21/62 |
| WO | WO 90/11511 | 10/1990 | ......... G01N/21/76 |
| WO | WO 92/14138 | 8/1992 | ......... G01N/21/66 |

OTHER PUBLICATIONS

Blackburn, Gary F., et al., "Electrochemiluminescence Detection for Development of Immunoassays and DNA Probe Assays for Clinical Diagnostics," Clinical Chemistry 37/9:1534–1539 (1991).

Hoyle, N. R., "The Application of Electrochemiluminescence to Immunoassay–Based Analyte Measurement," Bioluminescence and Chemiluminescence—Fundamentals and Applied Aspects, Proceedings of the 8th International Symposium on Bioluminescence and Chemiluminescence, Cambridge, Sep. 1994 (3pp).

(List continued on next page.)

Primary Examiner—Long V. Le
Assistant Examiner—Jacob J. Cheu
(74) Attorney, Agent, or Firm—McDonnell Boehnen Hulbert & Berghoff

(57) ABSTRACT

A method for analyzing a liquid test sample by electrochemiluminescence. The method includes at least one specific biochemical binding reaction that leads to the formation of a complex which contains a chemiluminescence marker and the binding of the complex to a magnetic microparticle. Detection is carried out in a measuring cell having a working electrode in order to determine the concentration of the marked microparticle. The detection cycle includes a purification step, a conditioning step, a recovery step and a measuring step. A specified potential profile is applied to the working electrode during these steps. Between the conditioning step and the recovery step, an additional potential pulse with an oxidizing and/or a reducing potential is inserted into the voltage shape of the detection cycle in order to improve the deposit of the microparticle.

14 Claims, 2 Drawing Sheets

OTHER PUBLICATIONS

Figure 1:
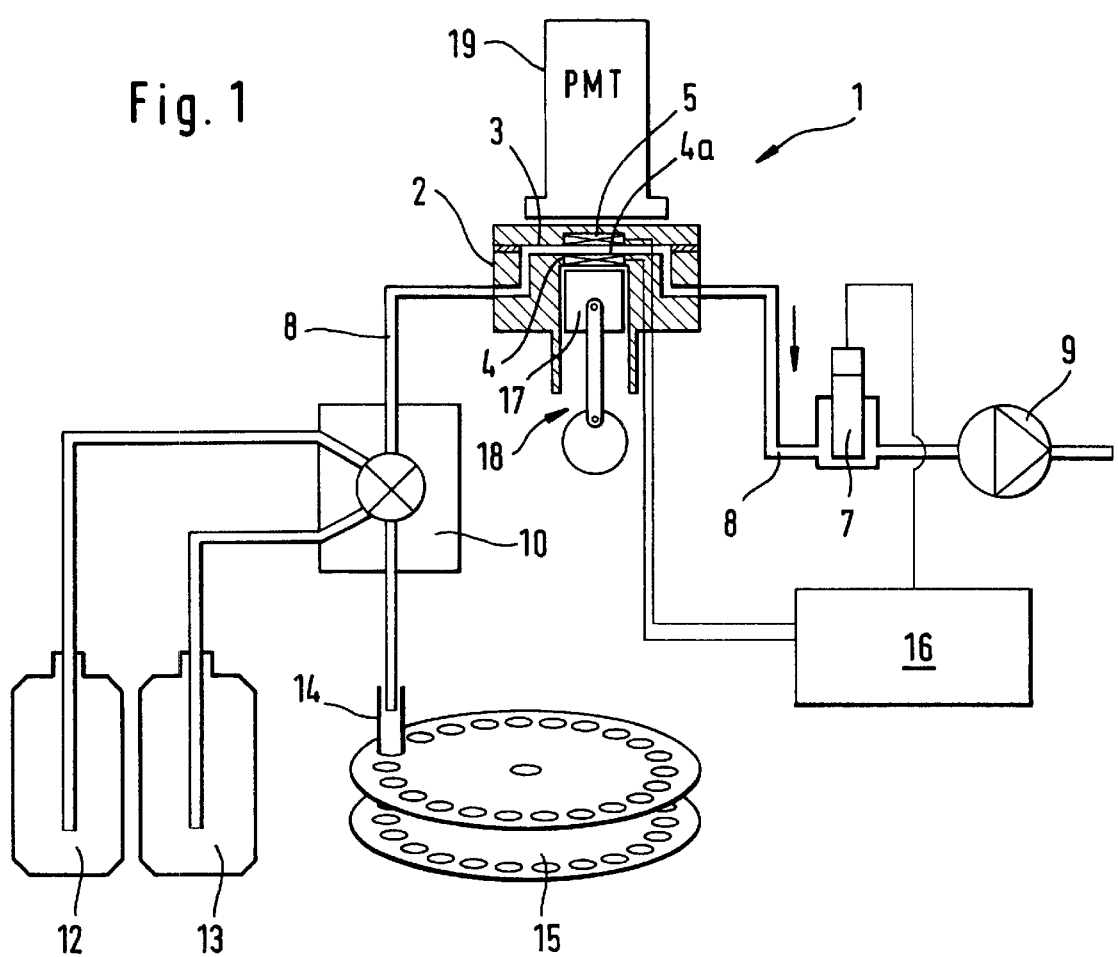

Kenten, J. H., et al., "Improved Electrochemiluminescent Label for DNA Probe Assays: Rapid Quantitative Assays of HIV–1 Polymerase Chain Reaction Products," Clinical Chemistry 38/6:873–879 (1992).

Leland, Jonathan K., et al., "Electrogenerated Chemiluminescence: An Oxidative–Reduction Type ECL Reaction Sequence Using Tripropyl Amine," Journal of Electrochemical Society 137/10:3127–3131 (1990).

* cited by examiner

ELECTROCHEMILUMISCENCE METHOD FOR DETECTING ANALYTES

The invention refers to a method for the analysis of a sample with regard to a substance contained therein.

The analysis of a liquid sample is generally concerned with the determination of the concentration of a substance (analyte) contained therein (quantitative analysis). In some cases, it is sufficient simply to determine whether the analyte is present (in a concentration exceeding a threshold value) in the sample or not (qualitative analysis). In medical applications for which the present invention is of particular importance, the analysis of body fluids (primarily blood, blood serum and urine) with regard to the analytes contained therein, such as hormones, antibodies, antigens or drugs, plays an important role.

The invention refers to the improvement of a certain type of analytic procedure which may be designated as an electrochemiluminescence binding reaction analysis (subsequently referred to as ECL-BBA standing for electrochemiluminescence biochemical binding analysis). Such a method has the following characteristic features.

a) The analytic selectivity is based on a specific biochemical binding reaction using biochemical substances which selectively can only bind to each other. Primary examples are immunological chemical binding reactions between antibodies and antigens or haptens with which the antibodies bind specifically. Other biochemical binding reactions are protein binding, in particular between avidine and biotin, the lectine carbohydrate binding, binding between receptors and ligands and the hybridization of nucleic acids.

Such specific biochemical binding reactions have been used for some time for analytic purposes. There are a plurality of differing one or multi-step reaction processes (test protocols) which finally lead, through the participation of the analyte and at least one specifically binding substance contained in the reagent system (binding reagents), to the formation of a complex characteristic for the analysis. This complex normally (but not necessarily) contains the analyte.

b) In order to render the complex, whose concentration constitutes a measure of the analytic result sought, detectable, a marking substances (label) is normally used which is coupled to a binding reagent of the reagent system, e.g. an antibody. The species comprising the marking substance and the binding reagent is designated as a conjugate.

The invention refers to cases in which the marking substance is capable of effecting an ECL-reaction. When such a substance is subjected to a suitable electrical potential on a voltametric electrode, it emits light which can be measured photometrically. A second electrochemically active substance, designated as a precursor, normally contributes to this reaction. In practice, primarily a ruthenium complex (ruthenium-tris [bipyridyl]) is used as ECL-label in combination with TPA (tripropylamine) as precursor. The two electrochemically active substances react on the electrode each releasing an electron and thereby forming a strongly reducing or oxidizing species. The subsequent redox reaction brings the ECL-label into an excited state from which it returns to the ground state with the emission of a photon. The ECL-label reaction is preferably a circular reaction so that a single label molecule emits a plurality of photons after application of a voltage to the electrode.

c) In the methods to which the invention refers, the ECL-marked complex molecules characteristic for the analysis are fixed to magnetic microparticles (beads). In practice, magnetized polystyrol balls having a diameter of typically 2 to 3 $\mu$m are used. Fixing is effected by means of a pair of specific biochemical binding partners. The pair streptavidin biotin has turned out to be particularly advantageous. The beads are coated with a streptavidin polymer. Biotin is bound to the complex molecule.

The beads with the bound marked complex are introduced into the measuring cell of a measuring apparatus. The cell is equipped the electrodes (normally a working electrode, a counter electrode and, in particular for the case of a potentiometric measurement scheme, a reference electrode) which are, necessary for generating the electrical field required for triggering the ECL-reaction. The beads are drawn onto the surface of the working electrode in the magnetic field of a magnet disposed below the working electrode. Since this normally occurs in flow-through cells with continuously flowing sample fluids, the magnetic deposition of the beads is designated as "capturing".

Generally after the capturing step a washing step is carried out during which a washing fluid flows by the working electrode to remove unwanted components. An electric potential required for triggering the ECL-reaction is then applied to the working electrode and the resulting luminescence light is measured using a suitable optical detector. The intensity of the luminescence light is a measure for the concentration of the marked beads on the surface of the working electrode which, in turn, is a measure of the concentration of the analyte in the sample. A calibration allows calculation of the sought concentration from the measured luminescence signal.

A plurality of different variations of this type of ECL-BBA-method have been discussed and described in the literature. Such variations may refer to each of the individual aspects mentioned.

With regard to aspect a), the tests are distinguished from each other by different test protocols (for example sandwich tests and competitive tests, each with a plurality of different sub-variations). A fundamental difference obtains between homogeneous tests which do not require separation between the formed complex molecules and the non-complexed conjugate and heterogeneous tests which require such a bound/free separation. The present invention can be used for very differing test protocols as long as they include a reaction sequence which comprises at least one specific chemical binding reaction and which leads to the formation of a complex which is characteristic of the analysis and which is marked with an ECL-label.

Also with regard to aspect b) the invention is universally applicable, i.e. it is independent of the ECL-label used and possible additional components of the ECL-reaction. The invention has turned out to be particularly usefully for test methods using the mentioned ruthenium complex in combination with TPA.

With regard to aspect c), the invention is solely directed to tests in which the complex characteristic for the analysis is bound to magnetic microparticles and in which these microparticles are deposited on the surface of a working electrode in the magnetic field of the magnet. The invention is otherwise independent of variations of aspect c) and can e.g. be used with differing bead materials and sizes as well as differing methods for fixing the complex to the beads.

More detailed information concerning the ECL-BBA-method can be taken from the extensive literature. Towards this end in particular the following publications are cited, the complete disclosure of which is hereby incorporated by reference:

1) G. F. Blackburn et al. "Electrochemiluminescence Detection for Development of Immunoassays and DNA Probe Assays for Clinical Diagnostics", Clin. Chem. 37 (1991), 1534–1539

2) J. K. Leland and M. J. Powell: "Electrogenerated Chemilumenescence: An Oxidative-Reduction Type ECL Reaction Sequence using Triprolyl Amine", J. Electrochem. Soc., 137(1990), 3127–3131

3) J. H. Kenten et al.: "Improved Electrochemiluminescent Label for DNA Probe Assays: Rapid Quantitative Assays of HIV-1 Polymerase Chain Reaction Products", Clin. Chem. 38 (1992), 873–879

4) N. R. Hoyle: "The Application of Electrochemiluminescence to Immunoassay-based Analyte Measurement" in "Bioluminescence and Chemilumenescense"; Proceedings of the 8$^{th}$ International Symposium on Bioluminescence and Chemilumenescence, Cambridge, September 1994, A. K. Campbell et al. (edit.), John Wiley & Sons

5) WO 89/10551

6) WO 90/11511

As mentioned, the measurement of the ECL-light is normally carried out in a flow-through measurement cell. The cell comprises a narrow flow channel for the sample fluid, and the working electrode is disposed on one of the walls defining the flow channel. In order to be able to sequentially measure differing samples with the same measuring cell, the cell, in particular the working electrode, must be cleaned between measurements to remove the beads and other impurities deposited thereon. This cleaning process must be rapid and efficient in order to guarantee a high throughput for the analysis apparatus and good analysis precision.

Cleaning is therefore not only done physically (passage of air bubbles) and chemically (passage of a cleaning fluid containing, inter alia, a detergent). Rather also electrochemical cleaning takes place by application of a strongly oxidizing and/or reducing potential to the working electrode. The potential is normally sufficiently high that gas bubbles are formed on the surface of the working electrode. This effectively supports the cleaning process. The electrochemical equilibrium of the electrode surface is, however, so strongly perturbed that after the cleaning step a conditioning step must be carried out in which a sequence of pulses are applied to the working electrode which cover the entire working potential range of the electrode material used.

Thus, a detection cycle is carried out in the cell which includes a sequence comprising a cleaning step, a conditioning step, a capturing step and a measuring step. During the cleaning step and during the conditioning step a cleaning fluid and a conditioning fluid respectively are located in the cell. The sample fluid with the beads is introduced into the flow-through measuring cell only at the beginning of the capturing step. Heterogeneous tests comprise an additional washing step between the capturing step and the measuring step. The detection cycle is explained in more detail in references 1 through 6, primarily in WO 89/10551.

The ECL-BBA-method is distinguished, in comparison to other analysis methods which are based on the specific binding of biochemical binding partners, by simple handling, high sensitivity, a large dynamic range of measurable concentrations, an economical analysis, and good automation possibilities (by means of corresponding analysis apparatus).

In order to achieve a further increase of the analytical precision of ECL-BBA-methods of the above mentioned type an additional potential pulse having an oxidizing and/or reducing potential is introduced, in accordance with the invention, into the voltage curve of the detection cycle between the conditioning step and the capturing step to improve deposition of the microparticles, wherein the additional potential pulse is returned to a neutral (neither oxidizing nor reducing) potential before the working electrode is contacted by the sample.

The dependence of the quality of the analysis on the voltage curve applied to the working electrode during the detection cycle is discussed in WO 89/10511 (reference 5). According to this reference, a constant potential value, designated as a "preoperative potential" should be applied at the end of the conditioning step in order to improve the reproducibility of the analysis result. This preoperative potential should remain constant until the working electrode is contacted by the sample fluid and the ECL-measurement is carried out. The preoperative potential should be either an oxidizing potential or a reducing potential in dependence on the material of the working electrode and on the electrolyte used.

In the context of the invention it has been discovered that, in contrast to the teaching of reference 5, a substantial improvement concerning the even deposition of the beads on the surface of the working electrode and thereby an improvement in the reproducibility and precision of the analysis can be achieved if the additional potential pulse is introduced into the voltage curve of the detection cycle. It is important that this pulse on the one hand attains an oxidizing or reducing potential value and on the other hand is returned to a neutral (neither oxidizing nor reducing) potential before the sample is introduced into the measuring cell and contacts the working electrode.

While the preoperative potential of WO 89/10551 is intended to influence the components of the sample pertinent to the generation of the ECL-signal, the invention achieves a substantial improvement by means of an additional electrochemical preprocessing of the electrode. The fact that this leads to an improvement in the deposition of the beads is unexpected, since it was to be assumed that the bead distribution depends on the properties of the magnetic field, whereas the electrochemical conditioning and cleaning measures serve for improvement of the signal generation.

A potential pulse as used in the invention is a transient change of the voltage applied to the working electrode during which an oxidizing or reducing potential value is reached, whereas the electric potential is in the neutral region before and after the potential pulse. The detailed shape of the potential curve may vary. It is in particular not necessary that the potential curve have a defined geometrical shape (e.g. rectangular, triangular or step function).

An oxidizing potential is an electric potential of the working electrode by which the surface thereof which is in contact with the conditioning fluid is oxidized. A potential is reducing when it effects an electrochemical reduction of the metallic surface of the working electrode in contact with the conditioning fluid. A potential by which practically no oxide or hydride layer is formed on a clean metallic surface is neutral. This state is also called the double-layer region of the corresponding metal.

No generally valid numerical values for the maximum potential of the additional pulse and for the value to which this potential must be returned can be given, since these potential values depend on the material of the working electrode, on the reference electrode to which the potential refers, and (to a lesser extent) on the composition of the conditioning liquid. Those skilled in the art can take more detailed information in this regard from published data in particular from cyclovoltamograms of the electrode material used. In any event, the values for an oxidizing, reducing, or neutral potential can be determined experimentally.

The invention is explained more closely below with regard to an embodiment schematically represented in the figures.

Figure 3:
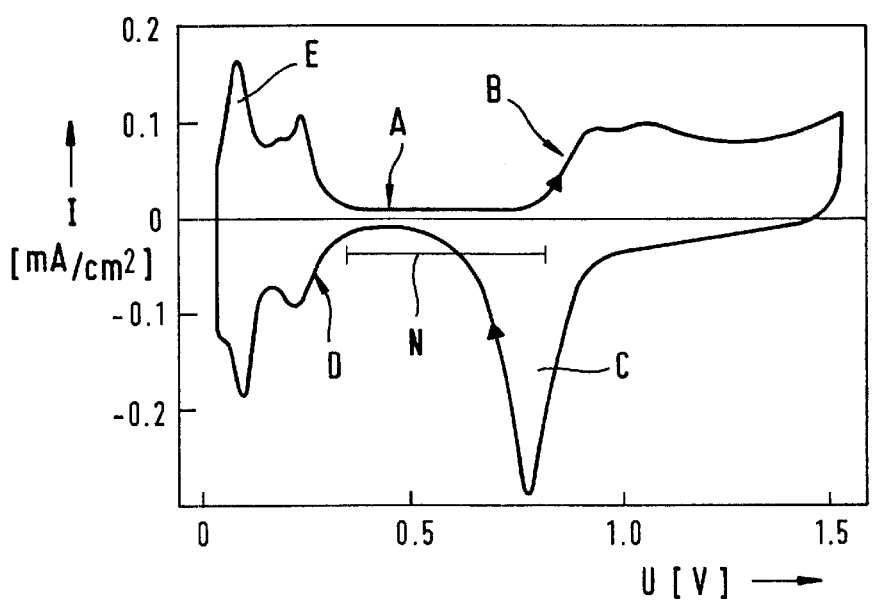
Figure 2:
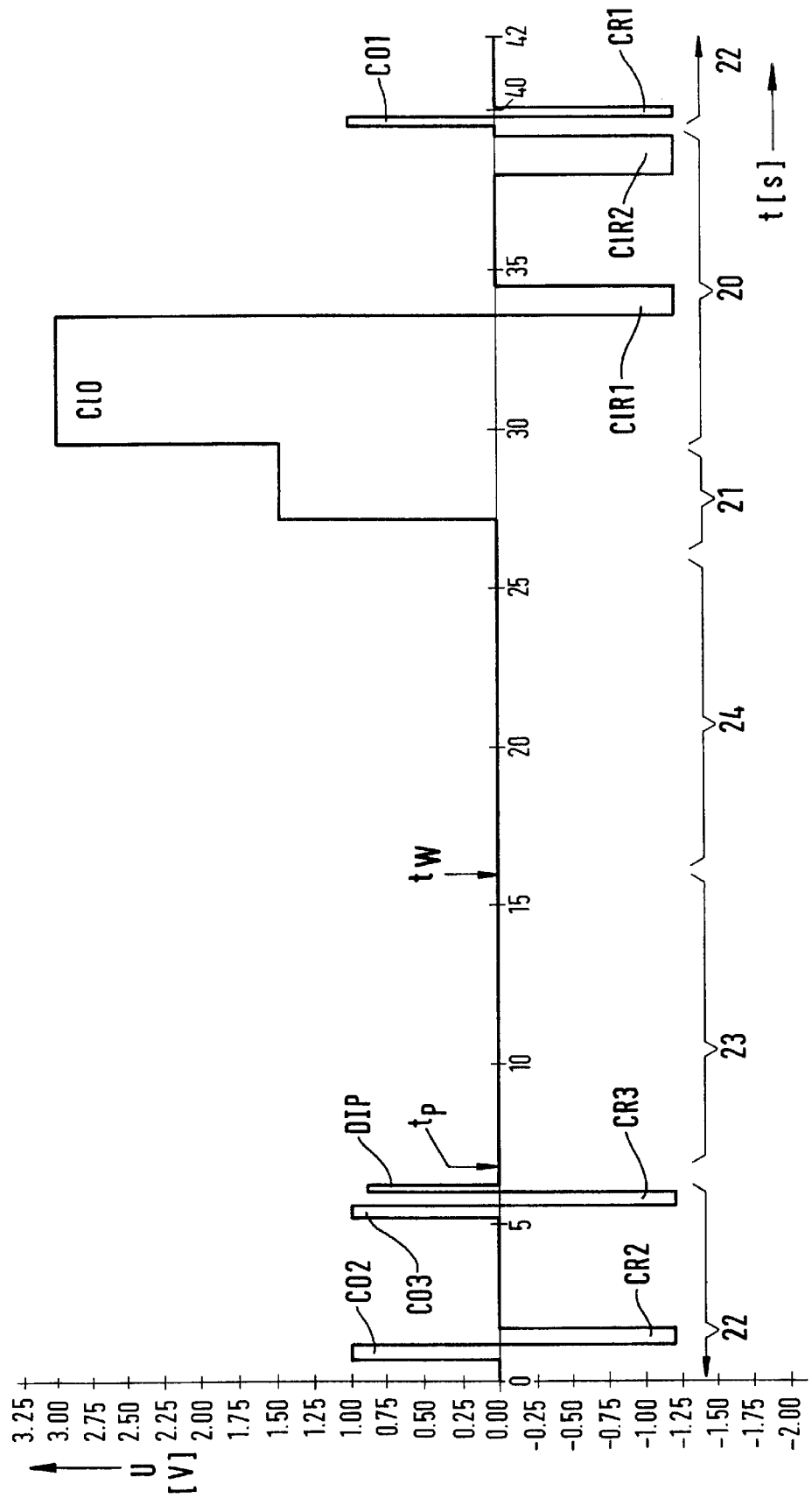

FIG. 1 shows a schematic representation of the detection unit of an ECL-BBA analysis apparatus, FIG. 2 shows a graphical representation of the time dependence of the potential applied to the working electrode during a detection cycle, FIG. 3 shows a cyclovoltamogram of a platinum electrode.

The detection unit 1 shown in FIG. 1 constitutes that part of the analysis apparatus which automatically carries out the detection cycle. In addition, such an analysis apparatus has units for carrying out the reaction sequence which leads to formation of a complex marked with an ECL-label (the concentration of which is characteristic for the analysis) and to its binding to magnetic microparticles. These components are not shown in FIG. 1.

The heart of the detection unit 1 is an electrochemical flow-through cell 2 in which a working electrode 4 and a counter electrode 5 are disposed at a narrow flow-through channel 3 in such a manner that they are contacted by a liquid flowing through the flow-through channel 3. The counter electrode 5 is, as shown, preferably positioned across from the working electrode 4 (i.e. at the opposite side of the flow-through channel 3). A reference electrode 7 is normally located at the liquid conduit of the detection unit 1, designated in its entirety with 8, outside of the flow-through channel 3. A precision reciprocating pump 9 is normally used for suctioning the liquid and is installed in the liquid conduit 8 downstream of the flow-through cell.

A plurality of liquid containers are connected to the conduit 8 upstream of the flow-through cell 2 from which liquid can be selectively suctioned into the flow-through cell 2 as controlled, e.g. by a multiple way valve 10. In the example shown, these are a container 12 having cleaning liquid, a container 13 having conditioning liquid, and a container 14 having sample liquid. The sample liquid container 14 is normally configured as a test tube (reaction tube) which is seated within a processing rotor 15 in which also the steps required for carrying out the binding reaction are performed. For reasons of clarity, only one of the reaction tubes seated in the processing rotor 15 is shown.

A magnet 17 is disposed in the flow-through measuring cell 2 at the side of the working electrode 4 facing away from the flow-through channel 3. In the example shown, a permanent magnet is used which can be moved by means of a movement mechanism 18 from the capturing position shown (in which at least one of its pole pieces is as close as possible to the working electrode 4) into a neutral position removed from the working electrode 4. An electromagnet which can be switched on and off can alternatively be used.

A photo-multiplier is used as a light detector 19 and is positioned on that side of the flow-through channel 3 lying across from the capturing surface 4a in such a manner that its light sensitive surface extends parallel to the capturing surface 4a of the working electrode 4 facing the flow-through channel 3 (and facing away from the magnet 17).

The elements of the detection unit 1 are connected to an electronics unit 16, provided for controlling the apparatus and processing the signals from the light detector 19 (the connecting cables are only partially shown).

It is important for the function of the detection unit 1 that the time dependence of the potential applied to the working electrode 4 (relative, in each case, to the liquid in contact therewith and thereby relative to the reference electrode) during the individual processing steps of a detection cycle have particular features which will now be described in more detail on the basis of the graphical representation of such a potential curve shown in FIG. 2. The figure relates to an embodiment having a platinum working electrode. The voltage values U given on the ordinate are measured relative to an Ag/AgCl-reference electrode and plotted against the time t in seconds. The detection cycle is repeated in the same manner for each analysis. The following description begins with the cleaning step.

A cleaning step 20 is carried out in each case following the preceding measurement in order to free the deposit surface 4a of the working electrode 4 from beads bonding thereto and other impurities or changes in the electrode surface. A strongly oxidizing and/or reducing potential ClO or ClR respectively is applied to electrochemically assist the cleaning process. Its potential value is generally higher than that of all other potentials in the detection cycle (both oxidizing and reducing). An oxidizing potential ClO is preferred —as shown —whose value exceeds a likewise oxidizing potential of the preceding measurement step 21. In the example shown, the cleaning step includes two smaller reducing potentials ClR1 and ClR2. This is, however, not absolutely necessary. The invention is suitable for all detection cycles in which during the cleaning step an oxidizing or reducing potential is applied to the working electrode which is so strong that a subsequent conditioning step is required to reestablish electrochemical equilibrium. A pump 9 feeds during the entire cleaning step cleaning fluid out of the container 12 through the conduit 8 and thereby also through the flow-through channel 3.

A subsequent conditioning step 22 serves to reestablish the required electrochemical equilibrium on the electrode surface following the cleaning step 20. Towards this end, a sequence of alternating reducing and oxidizing potential pulses are applied to the working electrode designated in FIG. 2 with C01, CR1, CO2, CR2, CO3 and CR3.

The sequence of conditioning pulses preferably comprises —as shown —an alternating sequence of oxidizing and reducing pulses, an even total number of reducing and oxidizing pulses being particularly preferred. The duration of each conditioning pulse is, in practice, less than 1 second. Values of less than 0.7 seconds and more than 0.1 seconds are preferred and the range between approximately 0.3 seconds and approximately 0.5 seconds has turned out to be particularly useful.

The invention is characterized by the introduction of an additional potential pulse into the voltage curve of the detection cycle, designated in FIG. 2 with DIP for "deposition improvement pulse". It is introduced after the conditioning step 22 and before the point of time designated in FIG. 2 as $t_p$ at which the sample is pumped out of the sample container 14 via the valve 10 into the flow-through channel 3 (so that the beads contained in the sample fluid are brought into contact with the working electrode 4). This additional pulse is high enough to attain an oxidizing or reducing potential value for a very short time duration which is nevertheless sufficient to electrochemically influence the electrode surface (preferably at least approximately 0.05 seconds and particularly preferred at least 0.1 seconds). It is furthermore important that the potential be returned to a neutral potential value (neither oxidizing nor reducing) before time $t_p$. The example of an oxidizing DIP shown, wherein it follows a preceding reducing potential pulse CR of the conditioning step 22, is particularly preferred.

Within the framework of the invention, it has been discovered that by means of the DIP the surface of the electrode is prepared in an optimal manner for the capturing step. Simultaneously the surface is adapted to the properties of the beads (e.g. surface properties, zeta potential, stickiness etc.). Experimental optimization of the DIP allows adjustment of the deposition pattern such that it optimally corresponds to the requirements of a ECL-detection procedure.

At time $t_p$ the magnet 17 is located in the capturing position shown in FIG. 1. Attracted by its magnetic field the microparticles flowing with the sample fluid through the flow-through channel 3 are deposited on the surface of the working electrode. During the capturing step 23 and also during the subsequent washing step 24 the working electrode potential is preferably —as shown —in the neutral range. In conventional methods, the working electrode is normally during these steps separated from the potentiostat and therefore does not have a defined potential. In accordance with WO 89/10551, the "preoperative potential", described therein, namely a constant oxidizing or reducing potential, should be applied to the working electrode 4 during this part of the detection cycle.

Aside from the potential of the working electrode, the capturing step 23, the washing step 24 and the subsequent measuring step 21 are carried out in conventional manner. The multiple way valve 10 is switched at time $t_w$ such that, instead of the sample liquid, the conditioning liquid which simultaneously serves as washing liquid for the bound/free separation is suctioned out of the container 13 and into the conduit 8.

Instead of the one additional potential pulse DIP, a plurality of additional potential pulses can also be introduced into the voltage curve of the detection cycle between the conditioning step 22 and the capturing step 23, in which case all DIPs are preferably either oxidizing or reducing. The total duration of time during which the one DIP or the plurality of DIPs are located in the oxidizing or reducing region should be at least 0.05 seconds in each detection cycle, preferably at least 0.1 seconds, and at most 1 second and preferably at most 0.3 seconds.

FIG. 3 shows a cyclic voltamogram of a platinum electrode. These types of measurements are usually carried out by varying the potential applied to the electrode, relative to a reference electrode, in a triangular fashion to thereby generate the shown current/voltage curves. The cyclic voltamogram shows results from the measurement of a platinum electrode in contact with a 1M-sulfuric acid solution. The voltage values on the abscissa are relative to a normal hydrogen electrode. The current flow I in $mA/cm^2$ is given along the ordinate.

If one follows the current voltage dependence departing from point A in the direction of the arrow, the potential is initially located in a region in which only an amount of current which can hardly be measured flows, associated with the charging up of a double layer. This region is referred to in the English language literature as the "double-layer region". The current flow increases strongly in curve region B. Here oxidizing potential values as used in the present invention are reached, i.e. the platinum surface is electrochemically oxidized. The area under the curve corresponds to the amount of charge needed for the oxidation.

Preferably, the working electrode is a platinum electrode and the highest value of the additional potential pulse (DIP) corresponds to a voltage of at least 0.6 V, preferably at least 0.8 V, relative to an Ag/AgCl reference electrode. Preferably, the voltage is at most 1.6 V, preferably at most 1.2 V, relative to an Ag/AgCl reference electrode.

When the voltage applied to the electrode decreases after achieving its maximum value (here approximately 1.5 V), the current flow is initially low, but then increases again in the region in which the oxide layer is removed (curve region C). After the oxide layer has been removed, the current again falls close to zero in the double-layer region until the voltage reaches a value which causes a reduction of the platinum (previously substantially pure). This rising in the curve region D indicates a reducing potential value in the sense of the present invention. The voltage region between the oxidizing and the reducing potential is designated as the neural region N. After the potential is reversed again at approximately 0.1 V, the reduction layer on the platinum surface is removed in curve region E.

EXAMPLE

Comparison tests were carried out with the Elecsys 2010 apparatus of Boehringer Mannheim GmbH to compare the results with and without DIP. The detection cycle thereby corresponded to FIG. 2. The experiments with DIP inncluded an additional oxidizing pulse of rectangular shape with a pule height of +0.9 V and a pulse duration of 0.2 sec. For a PSA test (PSA=prostrate specific antigen) the following values were obtained without DIP.

TABLE 1

| No. | Conc. ng/ml | N | MW | VK % |
|---|---|---|---|---|
| 1 | 0.00 | 11 | 1020.94 | 2.66 |
| 2 | 0.75 | 4 | 4957.80 | 2.00 |
| 3 | 2.97 | 2 | 16698.81 | 1.75 |
| 4 | 16.20 | 2 | 84445.07 | 2.10 |
| 5 | 75.10 | 2 | 398381.77 | 0.99 |
| 6 | 142.00 | 2 | 741512.39 | 1.62 |

With DIP the following values were obtained:

TABLE 2

| No. | Conc. ng/ml | N | MW | VK % |
|---|---|---|---|---|
| 1 | 0.00 | 11 | 1045.33 | 1.12 |
| 2 | 0.75 | 4 | 5874.34 | 0.63 |
| 3 | 2.97 | 2 | 2093.29 | 1.06 |
| 4 | 16.20 | 2 | 107626.88 | 1.26 |
| 5 | 75.10 | 2 | 497223.62 | 0.99 |
| 6 | 142.00 | 2 | 950228.61 | 0.26 |

The column titles are defined as follows:
Conc.: nominal concentration of the calibration sample used
N: number of measurements carried out
MW: average value of the measurement signal in arbitrary units
VK: variation coefficient of the signal in percent One notices that the DIP leads to a substantial improvement in the signal dynamics (the quotient between the highest and the lowest MW). With DIP, this value is 909 and thereby approximately 25% higher than without DIP (726). In addition, the precision, reflected by the magnitude of the variation coefficient VK, is substantially improved.

By means of visual observation and using video recordings during the analysis cycle, it has been determined that the beads are also deposited in a substantially more stable manner. Without DIP, the beads move during the washing step. This is disadvantageous for the measurement precision, particularly since it can cause loss of previously deposited beads from the working electrode.

What is claimed is:

1. An electrochemiluminescence method of detecting an analyte in a liquid sample, said method comprising:
   (a) carrying out a reaction sequence comprising at least one specific biochemical binding reaction to form a complex as a result of the concentration of the analyte in the liquid sample, said complex comprising a marking substance capable of effecting an electrochemiluminescence reaction, said complex further being bound to magnetic microparticles, and (b) carrying out a detection cycle in a measuring cell having a working electrode for determination of the concentration of said bound microparticles, said detection cycle including a sequence comprising;

(i) a cleaning step during which a strongly oxidizing and/or reducing potential is applied to said working electrode for electrochemical cleaning of said electrode, (ii) a conditioning step comprising applying a sequence of a number of alternating reducing and oxidizing potential pulses to said working electrode, wherein said sequence comprises a last pulse;

(iii) a capturing step during which said sample containing said microparticles is contacted with said working electrode in such a manner that said microparticles are attracted by the magnetic field of a magnet positioned on the side of said working electrode facing away from said sample, thereby being deposited on a surface of said working electrode facing said sample, and (iv) a measuring step during which a potential is applied to said working electrode to trigger said electrochemiluminescence reaction and the light emitted by said marking substance is measured to determine the concentration of said substance on said deposit surface of said electrode, thereby determining the analyte in the liquid sample, said method further comprising applying at least one additional potential pulse having an oxidizing or reducing potential into the voltage curve of the detection cycle between said conditioning step and said capturing step, wherein said additional potential pulse is returned to a neutral potential prior to contacting of said working electrode by said sample.

2. The method of claim 1, wherein the last potential pulse of said conditioning step preceding said additional potential pulse is a reducing potential pulse.

3. The method of claim 1, wherein said additional potential pulse is an oxidizing potential pulse.

4. The method of claim 1, wherein during said conditioning step, the number of said reducing potential pulses is equal to the number of said oxidizing potential pulses.

5. The method of claim 1, wherein said additional potential pulse has the same polarity as the potential triggering said electrochemiluminescent reaction during said measuring step and the highest value of said additional potential pulse is less than the highest value of the potential triggering said electrochemiluminescent reaction.

6. The method of claim 1, wherein said working electrode is a platinum electrode and the highest value of said additional potential pulse corresponds to a voltage of at least 0.6 V relative to a Ag/AgCl reference electrode.

7. The method of claim 1, wherein said working electrode is a platinum electrode and the highest value of said additional potential pulse corresponds to a voltage of at least 0.8 V relative to a Ag/AgCl reference electrode.

8. The method of claim 1, wherein the highest value of said additional potential pulse corresponds to a voltage of at most 1.6 V relative to an Ag/AgCl reference electrode.

9. The method of claim 1, wherein the highest value of said additional potential pulse corresponds to a voltage of at most 1.2 V relative to an Ag/AgCl reference electrode.

10. The method of claim 1, wherein a plurality of additional potential pulses are introduced into the voltage curve of the detection cycle between said conditioning step and said capturing step, wherein the last additional potential pulse is returned to a neutral potential prior to contacting of said working electrode by said sample.

11. The method of claim 1, wherein the total amount of time during which the at least one additional potential pulse is in the oxidizing or reducing potential region respectively is, in each detection cycle, at least 0.05 seconds.

12. The method of claim 1, wherein the total amount of time during which the at least one additional potential pulse is in the oxidizing or reducing potential region respectively is, in each detection cycle, at least 0.1 seconds.

13. The method of claim 1, wherein the total amount of time during which the at least one additional potential pulse is in the oxidizing or reducing potential region respectively is, in each detection cycle, at most 1 second.

14. The method of claim 1, wherein the total amount of time during which the at least one additional potential pulse is in the oxidizing or reducing potential region respectively is, in each detection cycle, at most 0.3 second.

* * * * *